(12) United States Patent
Deshpande

(10) Patent No.: US 11,278,422 B2
(45) Date of Patent: Mar. 22, 2022

(54) INTERVERTEBRAL SPINAL CAGE IMPLANT AND METHOD OF ASSEMBLING THE SAME

(71) Applicant: Vasudeva Rao Rajakumar Deshpande, Bangalore (IN)

(72) Inventor: Vasudeva Rao Rajakumar Deshpande, Bangalore (IN)

( * ) Notice: Subject to any disclaimer, the term of this patent is extended or adjusted under 35 U.S.C. 154(b) by 762 days.

(21) Appl. No.: 16/069,494

(22) PCT Filed: Sep. 28, 2017

(86) PCT No.: PCT/IB2017/055963
§ 371 (c)(1),
(2) Date: Jul. 11, 2018

(87) PCT Pub. No.: WO2019/016582
PCT Pub. Date: Jan. 24, 2019

(65) Prior Publication Data
US 2021/0205093 A1    Jul. 8, 2021

(30) Foreign Application Priority Data

Jul. 19, 2017   (IN) .............................. 201741025557

(51) Int. Cl.
*A61F 2/44*    (2006.01)
*A61F 2/30*    (2006.01)

(52) U.S. Cl.
CPC .. *A61F 2/4455* (2013.01); *A61F 2002/30433* (2013.01); *A61F 2002/30462* (2013.01);
(Continued)

(58) Field of Classification Search
CPC .......... A61F 2/44; A61F 2/4455; A61F 2/446; A61F 2/4465; A61F 2/447; A61F 2002/448; A61F 2002/4485
See application file for complete search history.

(56) References Cited

U.S. PATENT DOCUMENTS 5,522,899 A * 6/1996 Michelson .............. A61F 2/442
                                                   606/279
5,861,041 A * 1/1999 Tienboon .............. A61F 2/4455
                                                  623/17.16
(Continued)

FOREIGN PATENT DOCUMENTS

EP    2398424 B1    6/2011
WO   2003068113 A2   8/2003

OTHER PUBLICATIONS

Nuvasive Brigade Cage (http://www.spinecal.com/What's-New.php—Last visited on: Jul. 9, 2018).

*Primary Examiner* — Eric S Gibson
(74) *Attorney, Agent, or Firm* — Michael F. Krieger; Kirton McConkie

(57) ABSTRACT

An intervertebral spinal cage implant system is provided. The system includes a first cage element of the intervertebral spinal cage. The system also includes a second cage element of the intervertebral spinal cage. The system further includes wherein the first cage element and the second cage element are mechanically coupled through a first coupling element. The system further includes a plurality of tethering elements configured to be mechanically coupled to corresponding vertebral bodies through a plurality of second coupling elements, wherein a first tethering element is configured to couple the first cage element to a first side of the first vertebral body and the second tethering element is configured to couple the second cage element to a second side of the first vertebral body.

20 Claims, 3 Drawing Sheets

(52) U.S. Cl.
CPC ............... *A61F 2002/30578* (2013.01); *A61F 2002/30604* (2013.01); *A61F 2002/448* (2013.01); *A61F 2310/00017* (2013.01); *A61F 2310/00023* (2013.01)

(56) References Cited

U.S. PATENT DOCUMENTS

| | | | |
|---|---|---|---|
| 6,110,210 A * | 8/2000 | Norton | A61F 2/441 623/17.16 |
| 6,251,140 B1 * | 6/2001 | Marino | A61F 2/4455 623/17.11 |
| 9,549,821 B2 * | 1/2017 | Matsumoto | A61F 2/4455 |
| 9,687,356 B1 * | 6/2017 | Spangler | A61F 2/4611 |
| 9,770,341 B1 * | 9/2017 | Walsh | A61F 2/4455 |
| 9,795,492 B1 * | 10/2017 | Walsh | A61F 2/4455 |
| 9,901,456 B2 * | 2/2018 | Matsumoto | A61F 2/442 |
| 10,973,652 B2 * | 4/2021 | Hawkins | A61F 2/442 |
| 2002/0082700 A1 * | 6/2002 | Bianchi | A61F 2/446 623/17.16 |
| 2002/0099376 A1 | 7/2002 | Michelson | |
| 2002/0161443 A1 * | 10/2002 | Michelson | A61F 2/30749 623/17.11 |
| 2004/0249461 A1 * | 12/2004 | Ferree | A61F 2/4455 623/17.11 |
| 2007/0049943 A1 * | 3/2007 | Moskowitz | A61F 2/4611 606/279 |
| 2008/0249622 A1 * | 10/2008 | Gray | A61F 2/4455 606/86 A |
| 2008/0312742 A1 | 12/2008 | Abernathie | |
| 2009/0005870 A1 * | 1/2009 | Hawkins | A61F 2/442 623/17.11 |
| 2009/0157186 A1 * | 6/2009 | Magerl | A61F 2/4455 623/17.16 |
| 2010/0023128 A1 * | 1/2010 | Malberg | A61F 2/442 623/17.16 |
| 2010/0249935 A1 | 9/2010 | Slivka et al. | |
| 2011/0301710 A1 * | 12/2011 | Mather | A61F 2/4611 623/17.16 |
| 2012/0179260 A1 * | 7/2012 | Nottingham | A61F 2/4455 623/17.16 |
| 2013/0018467 A1 * | 1/2013 | Suh | A61B 17/8852 623/17.16 |
| 2013/0150970 A1 * | 6/2013 | Thaiyananthan | A61F 2/442 623/17.16 |
| 2013/0184823 A1 * | 7/2013 | Malberg | A61F 2/442 623/17.13 |
| 2013/0274884 A1 * | 10/2013 | Matsumoto | A61F 2/30771 623/17.16 |
| 2013/0274886 A1 * | 10/2013 | Matsumoto | A61F 2/442 623/17.16 |
| 2014/0114414 A1 * | 4/2014 | Abdou | A61F 2/447 623/17.16 |
| 2016/0045326 A1 | 2/2016 | Hansen et al. | |
| 2016/0051373 A1 * | 2/2016 | Faulhaber | A61F 2/4465 623/17.16 |

\* cited by examiner

INTERVERTEBRAL SPINAL CAGE IMPLANT AND METHOD OF ASSEMBLING THE SAME

CROSS-REFERENCE TO RELATED APPLICATION

This application is a National Stage of International Application No. PCT/IB2017/055963, filed on Sep. 28, 2017 and entitled "INTERVERTEBRAL SPINAL CAGE IMPLANT AND METHOD OF ASSEMBLING THE SAME" and complete Patent Application No. 201741025557, filed on Jul. 19, 2017 in India, which is incorporated herein in its entirety.

BACKGROUND

Embodiments of the present disclosure relate to spinal implants, and more particularly to, intervertebral spinal cage implant and method of using the same.

A vertebral spine is an axis of the skeleton on which all the body parts hang.

Vertebral bodies of the vertebral spine are separated by intervertebral discs. The Intervertebral discs act as joints but allow known degrees of flexion, extension, lateral bending, and axial rotation and translation. The intervertebral disc can be displaced or damaged due to trauma, disease, degenerative defects, or wear over an extended period of time. One result of such displacement or damage to the intervertebral disc causes chronic back pain.

Traditionally, a spinal fusion of damaged intervertebral disc is done by using a plating system or a rod screw system in combination with an intervertebral spine cage. However, such systems do not provide stabilization in all directions in a plane of a patient's intervertebral space. Moreover, such approaches lead to failure of the system, which results in instability of the intervertebral spine cage.

Furthermore, some advanced implants include the intervertebral spine cage and a plurality of screws for aligning and holding adjacent vertebral bodies in a fixed position with respect to one another. However, in such implants, the screws loosen over a period of time, which causes damage to soft tissues in the patient's body. Also, standalone cages have a potential risk of displacement from an intended original position, which results in undesirable outcomes.

In some other approaches, the plurality of screws are inserted between the vertebral bodies at specific angles. However, such screw insertions are complex and lead to increased probability of nerves damage. Furthermore, some implants employ a single screw for stabilizing the intervertebral spine cage inserted between the adjacent vertebral bodies. However, such an approach leads to a movement restriction of the patient's body. Moreover, some approaches utilize a single screw to fix the intervertebral spine cage to a vertebra. However, such approach results in instability of the intervertebral spine cage.

Hence, there is a need for an improved implant to address the aforementioned issues.

BRIEF DESCRIPTION

In accordance with one embodiment of the disclosure, an intervertebral spinal cage implant system is provided. The intervertebral spinal cage implant system includes a first cage element of the intervertebral spinal cage. The intervertebral spinal cage implant system also includes a second cage element of the intervertebral spinal cage. The intervertebral spinal cage implant system further includes wherein the first cage element and the second cage element are mechanically coupled through a first coupling element. The intervertebral spinal cage implant system further includes a plurality of tethering elements configured to be mechanically coupled to corresponding vertebral bodies through a plurality of second coupling elements, wherein a first tethering element is configured to couple the first cage element to a first side of a first vertebral body and the second tethering element is configured to couple the second cage element to a second side of the first vertebral body.

In accordance with another embodiment of the present disclosure, a method of assembling an intervertebral spinal cage implant is provided. The method of assembling an intervertebral spinal cage implant includes positioning a first cage element of the intervertebral spinal cage between a first vertebral body and a second vertebral body of the spine. The method of assembling an intervertebral spinal cage implant also includes positioning a second cage element of the intervertebral spinal cage between the first vertebral body and the second vertebral body of the spine. The method of assembling an intervertebral spinal cage implant further includes coupling the first cage element and the second cage element using a coupling element. The method of assembling an intervertebral spinal cage implant further includes fastening the first cage element and the second cage element to the first side of the first vertebral body and second side of the first vertebral body through a first tethering element and a second tethering element respectively.

DETAILED DESCRIPTION

Embodiments of the present disclosure relate to an intervertebral spinal cage implant system and method of using the same. The intervertebral spinal cage implant system includes a first cage element of the intervertebral spinal cage. The intervertebral spinal cage implant system also includes a second cage element of the intervertebral spinal cage. The intervertebral spinal cage implant system further includes wherein the first cage element and the second cage element are mechanically coupled through a first coupling element. The intervertebral spinal cage implant system further includes a plurality of tethering elements configured to be mechanically coupled to corresponding vertebral bodies through a plurality of second coupling elements, wherein a first tethering element is configured to couple the first cage element to a first side of a first vertebral body and the second tethering element is configured to couple the second cage element to a second side of the first vertebral body.

In the following specification and the claims, reference will be made to a number of terms, which shall be defined to have the following meanings. The singular forms "a", "an", and "the" include plural references unless the context clearly dictates otherwise.

Figure 1:
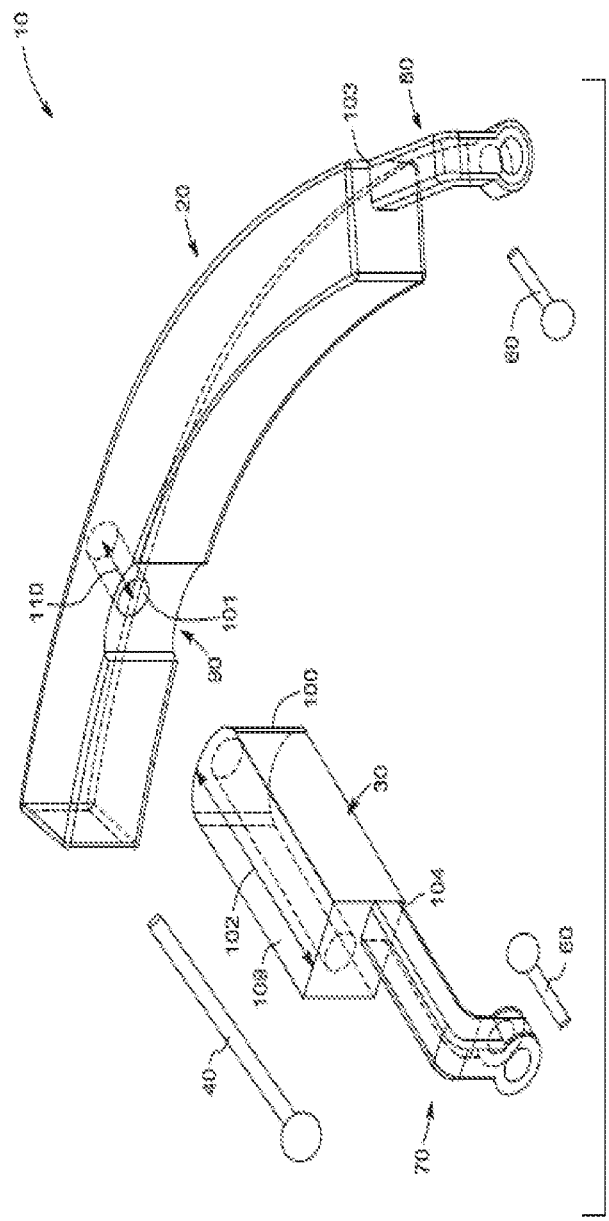
FIG. 1 illustrates a side view of an intervertebral spinal cage implant system in accordance with an embodiment of the present disclosure.

FIG. 1 illustrate the different views of an intervertebral spinal cage implant system (10) in accordance with an embodiment of the present disclosure. The intervertebral spinal cage implant system (10) includes a first cage element (20) of the intervertebral spinal cage implant system (10), a second cage element (30) of the intervertebral spinal cage implant system (10), wherein the first cage element (20) and the second cage element (30) are mechanically coupled through a first coupling element (40). The intervertebral spinal cage implant system (10) also includes a plurality of tethering elements (50)) configured to be mechanically coupled to a first vertebral body (FIG. 2) through a plurality of second coupling elements (60), wherein a first tethering element (70)) is configured to couple the first cage element (20) to a first side (FIG. 2) of the first vertebral body and the second tethering element (80)) is configured to couple the second cage element (30) to a second side (FIG. 2) of the first vertebral body.

In one embodiment, the first cage element (20) of the intervertebral spinal cage implant system (10) is of a curved shape. In another embodiment, the first cage element (20) of the intervertebral spinal cage implant system (10) may be an arch shape or any shape similar to the curve shape. In yet another embodiment, the second cage element (30) of the intervertebral spinal cage may include a cuboid shape. In another embodiment, second cage element (30) of the intervertebral spinal cage implant system (10) may be a rectangular shape or any other shape similar to the cuboid. The first cage element (20) and the second cage element (30) may be customized in various heights, sizes or geometry to fit the anatomical needs of a wide variety of patients.

In one embodiment, the first cage element (20) includes a first interlocking segment (90)) formed within the first cage element (20). In an exemplary embodiment, the first interlocking segment (90)) of the first cage element (20) may have a concave shape. Similarly, the second cage element (30) includes a second interlocking segment (100)) formed within the second cage element (30). In another embodiment, the second interlocking segment (100)) may have a convex shape.

Furthermore, such a configuration of the first interlocking segment (90)) and the second interlocking segment (100)) in the first cage element (20) and the second cage element (30) respectively enables interlocking of the first cage element (20) with the second cage element (30), when connected together. In other embodiments, the shapes of the first interlocking segment (90) and the second interlocking segment (100) may vary according to the shape of the first cage element (20) and the second cage element (30). In another embodiment, the first interlocking segment (90) and the second interlocking segment (100) may include one or more holes. The one or more holes are formed in the first interlocking segment (90)) and the second interlocking segment (100)) to couple the first cage element (20) and the second cage element (30) to each other. In yet another embodiment, a first end of the hole (101) of the first cage element (20) and a first end of the hole (102) of the second cage element (30) is configured to be aligned upon coupling of the first interlocking segment (90) and the second interlocking segment (100). In one embodiment, the first end of the hole of the first cage element and the first end of the hole of the second interlocking segment are aligned with each other using a guide wire.

The intervertebral spinal cage implant system (10) also includes a first coupling element (40) configured to couple the first cage element (20) and the second cage element (30). In one embodiment, the first coupling element (40) includes a screw. The size of the first coupling element (40) depends on the radius of the one or more holes in the first interlocking segment (90) and the second interlocking segment (100). The size of the first coupling element (40) also depends upon a length of the second cage element (30), which is represented by a first axis (109) and a width of the first cage element (20) represented by a second axis (110) respectively.

The intervertebral spinal cage implant system (10) further includes a plurality of tethering elements (50) configured to be mechanically coupled to the first vertebral body (FIG. 2) through a plurality of second coupling elements (60), wherein a first tethering element (70) is configured to couple the first cage element (20) to a first side (FIG. 2) of the first vertebral body and the second tethering element (80) is configured to couple the second cage element (30) to a second side (FIG. 2) of the first vertebral body. In one embodiment, a first end (103) of the first tethering element (70) and a first end (104) of the second tethering element (80) are fixed. In another embodiment, at least one of the first end (103) of the first tethering element (70) and the first end (104) of the second tethering element (80) is movable. In a specific embodiment, at least one of the first tethering element (70) and the second tethering element (80) may be flexible to adjust the first tethering element (70) and the second tethering element (80) as per the requirements of a Doctor. In such embodiments, the movement of the first end (103) of the first tethering element (70) and/or the first end (104) of the second tethering element (80) enables easy and customized coupling to the first cage element (20) and the second cage element (30) to the first vertebral body (105) respectively. The plurality of tethering elements (50) are coupled to the first vertebral body (105) through a plurality of second coupling elements (60). In one embodiment, the plurality of second coupling elements (60) includes one or more screws. In some embodiments, the sizes of the first coupling element (40) and the plurality of second coupling elements (60) may be same. In another embodiment, the size of the first coupling element (40) may be different than the size of the plurality of second coupling elements (60).

Furthermore, the intervertebral spinal cage implant system (10) is composed of any material that is conducive to fusion between the first vertebral body and the second vertebral body of the spine. In one embodiment, the intervertebral spinal cage implant system (10) is composed of a surgical titanium alloy. In another embodiment, the intervertebral spinal cage implant system (10) is composed of a PEEK material. In yet another embodiment, the intervertebral spinal cage implant system (10) is composed of a carbon fibre material. In another embodiment, the intervertebral spinal cage implant system (10) may be composed of stainless steel.

Figure 2:
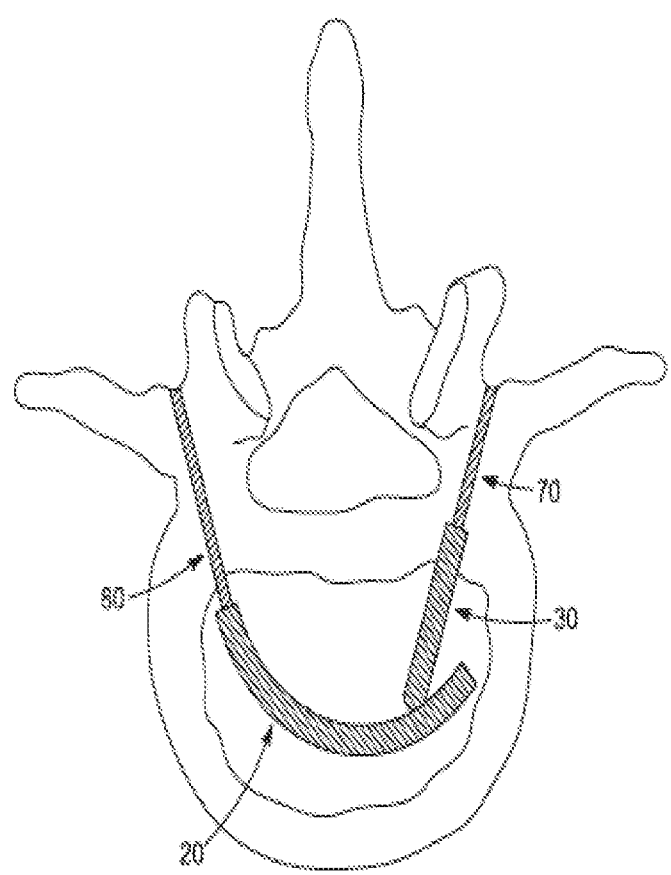
FIG. 2 illustrates a schematic representation of a vertebral section depicting an intervertebral spinal cage implant system located between a first vertebral body and a second vertebral body in accordance with an embodiment of the present disclosure.

FIG. 2 illustrates a schematic representation of an exemplary vertebral section depicting an intervertebral spinal cage implant system located between a first vertebral body and a second vertebral body in accordance with an embodiment of the present disclosure. The intervertebral spinal cage implant system (10) is placed between the first vertebral body (105) and the second vertebral body (106), which are adjacent to each other. Furthermore, the first cage element (20) and the second cage element (30) are placed between the first vertebral body (105) and the second vertebral body (106) of the spine such that the intervertebral spinal cage implant system (10) is located above the first vertebral body (105). The intervertebral spinal cage implant system (10) further includes a plurality of tethering elements (50) configured to be mechanically coupled to the first vertebral body (105) through a plurality of second coupling elements (60), where the first tethering element (70) is configured to couple the first cage element (20) to the first side (107) of the first vertebral body (105) and the second tethering element (80) is configured to couple the second cage element (30) to the second side (108) of the first vertebral body (105). Similarly, in other embodiments, the first cage element (20) and the second cage element (30) may be coupled to the second vertebral body also.

Figure 3:
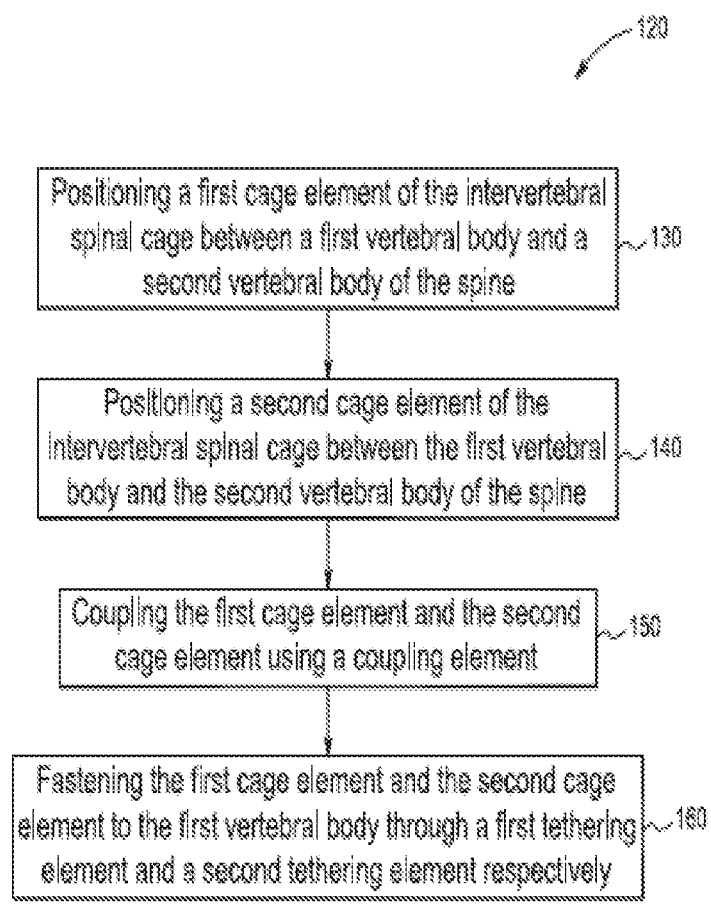
FIG. 3 illustrates a flow process representing steps involved in a method of assembling an intervertebral spinal cage implant in accordance with an embodiment of the present disclosure.

FIG. 3 illustrates a flow process representing steps involved in a method (120) of assembling an intervertebral spinal cage implant in accordance with an embodiment of the present disclosure. The method (120) includes positioning a first cage element of the intervertebral spinal cage implant system between a first vertebral body and a second vertebral body of the spine in step 130. The method (120) also includes positioning a second cage element of the intervertebral spinal cage implant system between the first vertebral body and the second vertebral body of the spine in step 140. In one embodiment, positioning the first cage element and the second cage element between the first vertebral body and the second vertebral body includes positioning the first cage element and the second cage element above the first vertebral body.

In another embodiment, the method (120) further incudes aligning one or more holes of a first interlocking segment of the first cage element and one or more holes of a second interlocking segment of the second cage element using a guide wire. Furthermore, the method (120) includes coupling the first cage element and the second cage element using a coupling element in step 150. In specific embodiment, coupling the first cage element and the second cage element through the first coupling element comprises inserting the first coupling element through a second end of the hole of second cage element towards a first end of the hole of the first cage element via a first end of the hole of the second cage element.

Furthermore, the method (120) includes fastening the first cage element and the second cage element to the first vertebral body through a first tethering element and a second tethering element respectively in step 160. In one embodiment, fastening the first cage element and the second cage element to the first vertebral body using the first tethering element and the second tethering element respectively comprises adjusting a position of the first tethering element and the second tethering element corresponding to the first vertebral body. In another embodiment, the first cage element and the second cage elements may couple to the second vertebral body. In yet another embodiment, the second end of the first tethering element and the second end of the second tethering element are coupled to the first side of the first vertebral body and the second side of the second vertebral body respectively using the plurality of second coupling element. The plurality of second coupling elements may include a plurality of plates which helps the plurality of second coupling elements to couple first tethering element and the second end of the second tethering element.

The intervertebral spinal cage implant system is designed to be conformable to the spinal anatomy, so as to be generally less intrusive to surrounding tissue and vasculature than existing rigid stabilization systems. The intervertebral spinal cage implant system provides the better stability than the conventional implant system as the plurality of tethering elements are connected to the single vertebral body. The intervertebral spinal cage implant system does not cause damage to soft tissues in the patient's body after a period of time, as the first coupling element is used to couple the first cage element and the second cage element rather than the vertebral bodies as in conventional implant systems.

It is to be understood that a skilled artisan will recognize the interchangeability of various features from different embodiments and that the various features described, as well as other known equivalents for each feature, may be mixed and matched by one of ordinary skill in this art to construct additional systems and techniques in accordance with principles of this disclosure. It is, therefore, to be understood that the appended claims are intended to cover all such modifications and changes as fall within the true spirit of the invention.

The invention claimed is:

1. An intervertebral spinal cage implant system comprising:
   a first cage element of the intervertebral spinal cage;
   a second cage element of the intervertebral spinal cage;
   wherein the first cage element and the second cage element are mechanically coupled through a first coupling element; and
   a plurality of tethering elements extending posteriorly from each of the first cage element and the second cage element and configured to be mechanically coupled to a posterior portion of a first vertebral body through a plurality of second coupling elements, wherein a first tethering element is configured to couple the first cage element to a first side of the first vertebral body and a second tethering element is configured to couple the second cage element to a second side of the first vertebral body.

2. The intervertebral spinal cage implant system as claimed in claim 1, wherein the first cage element of the intervertebral spinal cage comprises a curved shape.

3. The intervertebral spinal cage implant system as claimed in claim 1, wherein the second cage element of the intervertebral spinal cage comprises a cuboid shape.

4. The intervertebral spinal cage implant system as claimed in claim 1, wherein the first cage element comprises a first interlocking segment and the second cage element comprises a second interlocking segment.

5. The intervertebral spinal cage implant system as claimed in claim 4, wherein the first interlocking segment of the first cage element comprises a concave shape and the second interlocking segment of the second cage element comprises a convex shape.

6. The intervertebral spinal cage implant system as claimed in claim 4, wherein the first interlocking segment and the second interlocking segment comprise one or more holes.

7. The intervertebral spinal cage implant system as claimed in claim 6, wherein a first end of a hole of the first cage element and a first end of a hole of the second cage element are configured to be aligned upon coupling of the first interlocking segment and the second interlocking segment.

8. The intervertebral spinal cage implant system as claimed in claim 1, wherein the first coupling element and the plurality of second coupling elements comprise one or more screws.

9. The intervertebral spinal cage implant system as claimed in claim 1, wherein a first end of the first tethering element and a first end of the second tethering element are fixed.

10. The intervertebral spinal cage implant system as claimed in claim 1, wherein at least one of a first end of the first tethering element and a first end of the second tethering element are movable.

11. The intervertebral spinal cage implant system as claimed in claim 1, wherein the intervertebral spinal cage is composed of a surgical titanium alloy, a PEEK material, a stainless steel, a carbon fibre or any other materials used for implants.

12. The intervertebral spinal cage implant system as claimed in claim 1, wherein the first cage element comprises an elongate structure extending between a posterior end affixed to the first tethering element and an anterior end.

13. The intervertebral spinal cage implant system as claimed in claim 12, wherein the second cage element is mechanically coupled to the first cage element at a point on the first cage element anterior from a central point of the first cage element.

14. The intervertebral spinal cage implant system as claimed in claim 1, wherein the second cage element comprises an elongate structure extending between a posterior end affixed to the second tethering element and an anterior end, and wherein the second cage element comprises a hole extending between the posterior end and the anterior end, the hole adapted to receive the first coupling element therethrough.

15. The intervertebral spinal cage implant system as claimed in claim 1, wherein the posterior portion of the first vertebral body is a pedicle thereof.

16. A method of assembling an intervertebral spinal cage implant comprising:
    positioning a first cage element of the intervertebral spinal cage implant, the first cage element having a first tethering element extending posteriorly therefrom, between a first vertebral body and a second vertebral body of the spine;
    positioning a second cage element of the intervertebral spinal cage implant, the second cage element having a second tethering element extending posteriorly therefrom, between the first vertebral body and the second vertebral body of the spine;
    coupling the first cage element to the second cage element using a coupling element; and
    fastening the first cage element and the second cage element to a posterior portion of the first vertebral body through posterior portions of the first tethering element and the second tethering element, respectively.

17. The method as claimed in claim 16, wherein positioning the first cage element and the second cage element between the first vertebral body and the second vertebral body comprises positioning the first cage element and the second cage element above the first vertebral body.

18. The method as claimed in claim 16, further comprising aligning one or more holes of a first interlocking segment of the first cage element and one or more holes of a second interlocking segment of the second cage element using a guide wire.

19. The method as claimed in claim 18, wherein coupling the first cage element and the second cage element through the coupling element comprises inserting the coupling element through a second end of the hole of second cage element towards a first end of the hole of the first cage element via a first end of the hole of the second cage element.

20. The method as claimed in claim 16, wherein fastening the first cage element and the second cage element to the first vertebral body using the first tethering element and the second tethering element respectively comprises adjusting a position of the first tethering element and the second tethering element corresponding to the first vertebral body.

* * * * *